United States Patent
Nissilä

(10) Patent No.: US 7,160,253 B2
(45) Date of Patent: Jan. 9, 2007

(54) METHOD AND DEVICE FOR MEASURING STRESS

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 462 days.

(21) Appl. No.: 10/683,450

(22) Filed: Oct. 10, 2003

(65) Prior Publication Data

US 2004/0111036 A1    Jun. 10, 2004

(30) Foreign Application Priority Data

Nov. 8, 2002   (FI) ................................. 20022009

(51) Int. Cl.
*A61B 5/00*    (2006.01)
(52) U.S. Cl. .................... 600/500; 600/26; 600/300; 600/301; 600/509; 600/546
(58) Field of Classification Search ................ 600/509, 600/322, 323, 500–503
See application file for complete search history.

(56) References Cited

U.S. PATENT DOCUMENTS

| | | | |
|---|---|---|---|
| 4,683,891 A * | 8/1987 | Cornellier et al. | 600/301 |
| 5,267,568 A | 12/1993 | Takara | |
| 5,718,235 A * | 2/1998 | Golosarsky et al. | 600/515 |
| 6,293,904 B1 | 9/2001 | Blazey et al. | |
| 6,306,077 B1 | 10/2001 | Prabhu et al. | |
| 6,390,979 B1 | 5/2002 | Njemanze | |
| 6,754,524 B1 * | 6/2004 | Johnson, Jr. | 600/544 |
| 6,836,681 B1 * | 12/2004 | Stabler et al. | 600/515 |
| 2002/0007105 A1 | 1/2002 | Prabhu et al. | |

FOREIGN PATENT DOCUMENTS

WO    WO 96/20640    7/1996

OTHER PUBLICATIONS

Takahashi, Masaya; Heihachiro, Arito: "Effects of Single and Repeated Cognitive Tasks on Automatic Balance as Observed by an Analysis of R-R Intervals", European Journal of Applied Physiology and Occupational Physiology, Germany, vol. 72, No. 4, pp. 316-322 (1996).
European Search Report for European Application No. EP 03 10 4070.

* cited by examiner

*Primary Examiner*—Charles A Marmor, II
*Assistant Examiner*—Karen E Toth
(74) *Attorney, Agent, or Firm*—Hoffmann & Baron, LLP

(57) ABSTRACT

The invention relates to a method and an electronic device for implementing the method for measuring mental load. The electronic device generates at least two different cognitively loading tasks for the person participating in the measurement, the first task determining a reference level and at least one other task determining the loading capacity level. The electronic device determines the pulse parameters of the person participating in the measurement during the cognitively loading tasks. The electronic device also compares the pulse parameters during the different tasks with each other. Finally, the electronic device generates a value descriptive of the mental load of the person participating in the measurement on the basis of the comparison of the pulse parameters.

19 Claims, 4 Drawing Sheets

METHOD AND DEVICE FOR MEASURING STRESS

CROSS-REFERENCE TO RELATED APPLICATION

This application claims priority based on Finnish Patent Application No. 20022009, filed on Nov. 8, 2002.

1. Field of the Invention

The invention relates to a method and a device for measuring mental load.

2. Brief Description of the Related Art

Stress refers to an individual's physical and particularly mental load, to which the organism tries to adapt by using defense mechanisms. Stress is a state of load, where the resources required for adaptation are at least instantaneously exceeded. Modern man's most important cause of stress is mental load, which is affected for instance by social relations, changes in life, work, etc. A stressed individual's organism is as if under constant threat, whereby the adrenal gland secretes adrenalin, which increases the pulse rate, the blood pressure and accelerates the metabolism, for example. Although stress is a part of life, it may directly or indirectly cause the outbreak of many diseases if it continues for long.

Since stress affects an individual's wellbeing and health very comprehensively, different solutions have been developed for measuring it. One way of measuring stress is to use enquiries, wherein different questions are used to shed light on for instance the emotional state, mood, daily problems and causes of happiness, the experienced stress level, etc. The problem in the test is that it is subjective and not repeatable nor comparable with other tests.

Measurements of electro-dermal activity and the hormone content of skin have been made to determine stress. However, these measurements are individual and do not provide unambiguous and repeatable values.

Attempts have also been made to measure stress and mental load by means of the heart rate. Heart rate measurements have been made while loading a test subject with physically or cognitively demanding tasks. A physical task is an experiment causing orthostatic stress, wherein the heart rate is measured when the test subject is first sitting down and then stands up. The measurement is particularly directed to measuring the variation in the heart rate. The variation in the heart rate is greater when sitting down than when standing up. Although mental load or other stress, unrelated to the task, could affect the result of the experiment, a mere orthostatic experiment is not sufficient to determine the magnitude or actual effect of mental load or general stress.

Cognitively loading experiments include e.g. orientation tasks (e.g. the Cued Target Detection Task), the Stroop Task, tasks based on the use of memory (e.g. the Memory Search Task) and tasks requiring the observation of two things (e.g. the Double Task). In orientation and Stroop tasks, the time is measured that the person participating in the experiment needs to give the correct answer. However, habituation to the tasks affects reaction time, and the results of the tasks are not comparable with other tasks. In addition, these tasks also show the same problem as tasks employing physical load, i.e. the tasks cannot be used to determine the magnitude of mental load or general stress, although mental load or other stress that is unrelated to the task is known to affect the result of the experiment.

SUMMARY OF THE INVENTION

The object of the invention is to provide an improved method and an electronic device implementing the method, for determining mental load. This is achieved by a method of measuring mental load, in which method at least one pulse parameter is measured by means of an electronic device. Further in the method, the electronic device is used to generate at least two different cognitively loading tasks for the person participating in the measurement, the first task determining a reference level and at least one other task determining the loading capacity level; determine at least two pulse parameters related to different cognitively loading tasks for the person participating in the measurement; compare the pulse parameters during the different tasks with each other; and generate a value descriptive of the mental load of the person participating in the measurement on the basis of the pulse parameter comparison.

The invention also relates to an electronic device for measuring mental load, the electronic device comprising a heart rate monitor including means for measuring at least one pulse parameter. The electronic device further comprises means for loading the person to be measured with at least two different cognitively loading tasks, the first task determining a reference level and at least one other task determining the loading capacity level; and the electronic device is arranged to determine at least two pulse parameters related to different cognitively loading tasks for the person participating in the measurement; and compare the pulse parameters during the different tasks with each other; and generate a value descriptive of the mental load of the person participating in the measurement on the basis of the pulse parameter comparison.

Preferred embodiments of the invention are described in the independent claims.

The invention is based on performing at least two different cognitively loading tasks, the pulse being measured during the tasks, and the pulse measured being used to generate a pulse parameter. The amount by which the pulse parameters measured during the different tasks deviate from each other is indicative of mental load and stress unrelated to the tasks.

The method and electronic device of the invention bring about a plurality of advantages. The measurement is simple to make, since it operates in the same way as a simple game program, and gives a reliable and repeatable result of mental load.

BRIEF DESCRIPTION OF THE DRAWINGS

In the following, preferred embodiments of the invention will be described in detail with reference to the accompanying drawings, in which.

DETAILED DESCRIPTION OF THE PREFERRED EMBODIMENTS

The solution presented is particularly suitable for measuring mental load.

Figure 1:
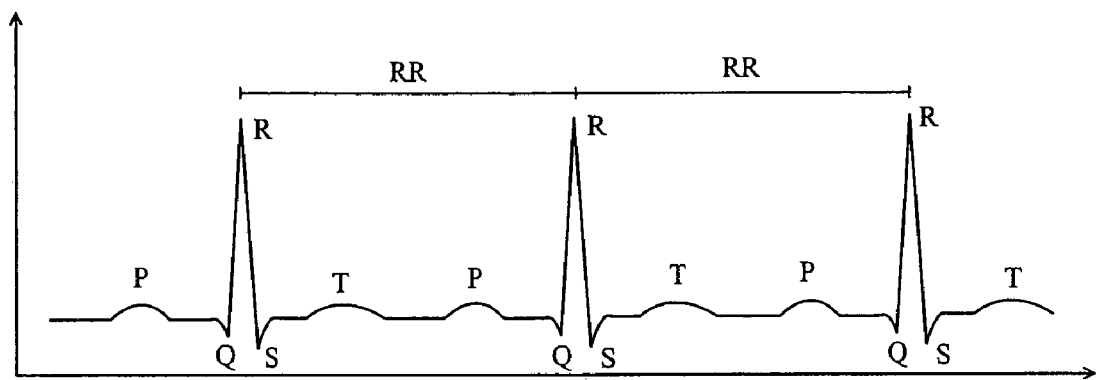
FIG. 1 shows an ECG signal.

Let us first study FIG. 1 showing an ECG signal caused by the pulse. The horizontal axis shows time and the vertical axis voltage. Repeating P, Q, R, S and T waves are distinguishable from the signal. The peak value R represents the maximum point of the ECG signal, and the pulse defined by the Q, R and S points, i.e. the so-called QRS complex, is the most easily recognizable part of the ECG signal, caused by ventricular contraction. The space between two successive R peaks is called the RR interval of the ECG signal.

Mental load causes changes in the operation of the autonomous nervous system. Due to variations in the sympathetic-parasympathetic balance of the autonomous nervous system, continuous fluctuations around the average pulse level occur in the heart rate, i.e. the length of the RR interval continuously changes. Pulse variation is caused by e.g. respiratory arrhythmia, variation caused by blood pressure regulation and variation caused by temperature regulation in the organism, which are also affected by stress. The most important of these is respiratory arrhythmia, which causes the most variation. Pulse variation frequency analysis can be used to distinguish between the heart rate variation transmitter nervous systems. The sympathetic nervous system is quite slow and almost incapable of transferring frequencies exceeding 0.15 Hz. The operation of the parasympathetic nervous system, in turn, is rapid, wherefore frequencies exceeding the above limit frequency are transferred via the parasympathetic nerves.

Pulse variation can be measured by means of the standard deviation, for example. Other generally used measurement units for the variation include the effective values of spectral calculation, the maximum value of variation and the height of the scatter diagram. The standard deviation does not separate the frequency components of the time intervals between the peaks of the R wave, i.e. the RR intervals, but it is affected by frequencies transferred from both autonomous nervous systems. The short-term standard deviation of the RR intervals almost exclusively measures the portion of parasympathetic regulation in the pulse variation.

When the loading level is raised from the rest level, the parasympathetic tonus first drops stepwise. When the exertion is low, a raise in the pulse almost completely results from decreased parasympathetic activity. The variation in the pulse then decreases relative to the exclusion of parasympathetic control.

Figure 2:
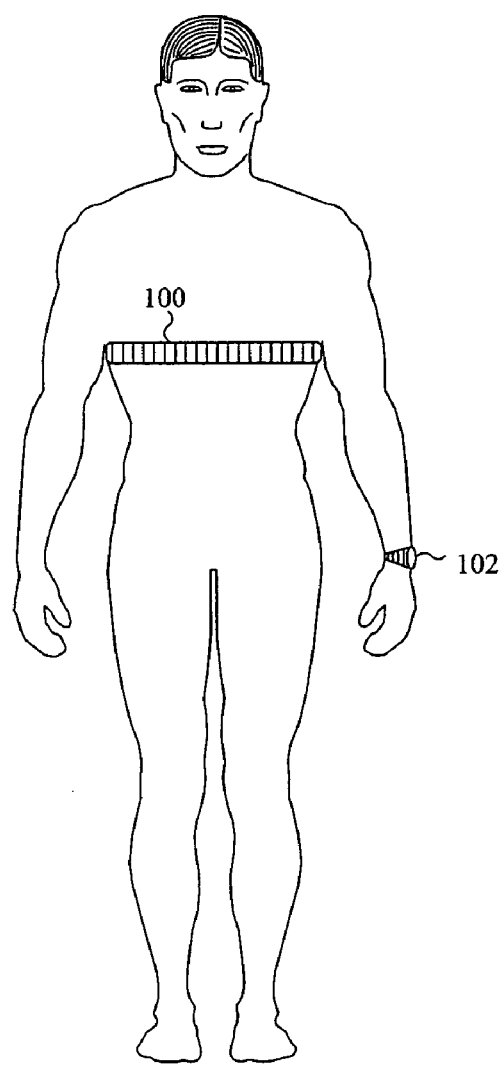
FIG. 2 shows a heart rate monitor on a person participating in a measurement.

Let us now study the solution presented by means of FIG. 2. A heart rate monitor comprises a transmitter unit 100 fastened around the chest for measuring the pulse. In addition, the user may have a receiver unit 102 for the heart rate monitor around the wrist.

Figure 3:
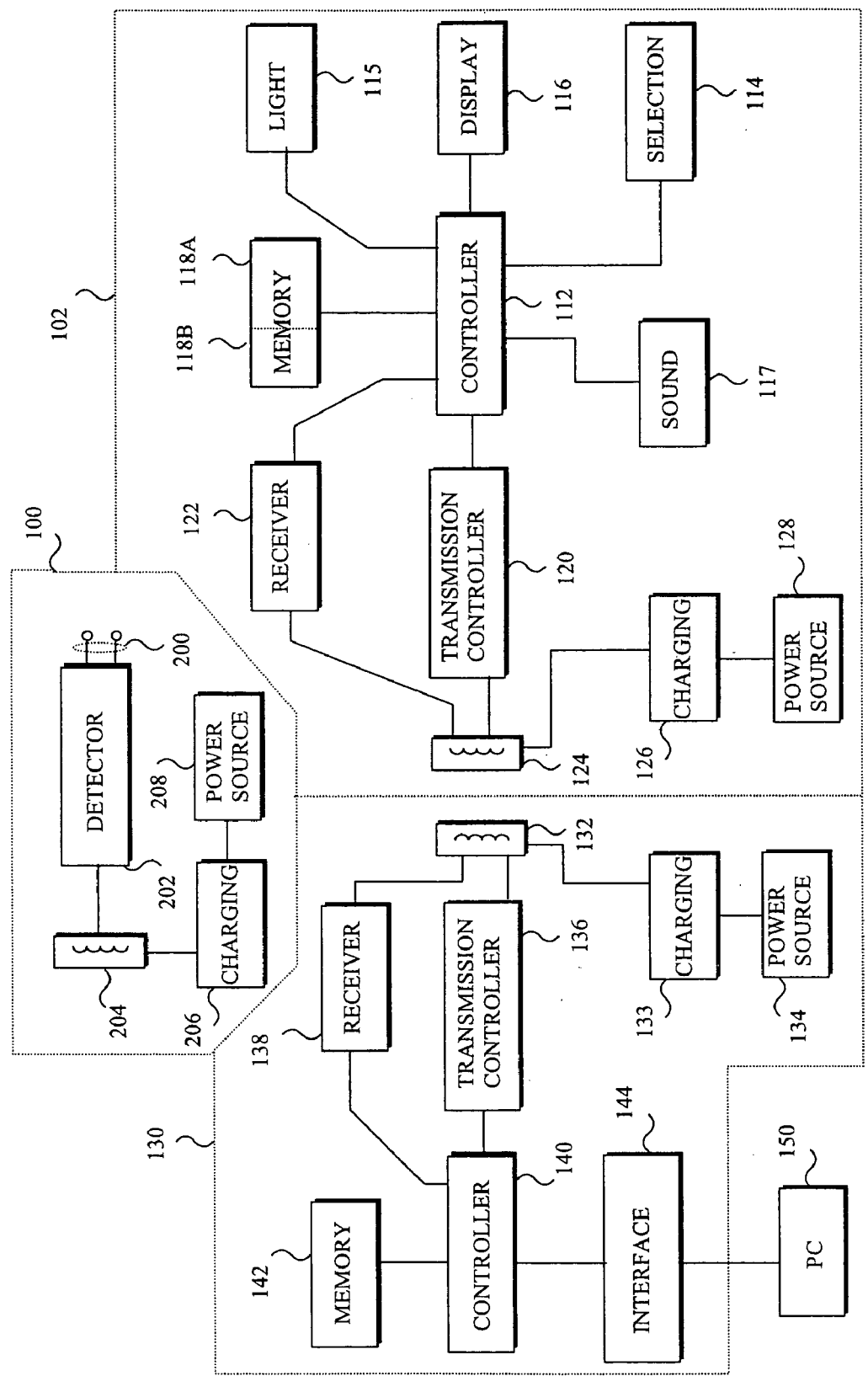
FIG. 3 is a block diagram of an electronic device.

Let us now study the electronic device associated with the pulse measurement more closely by means of FIG. 3. The main parts of the arrangement include a telemetric transmitter unit 100 and a telemetric receiver unit 102, which constitute the main parts of the heart rate monitor. In addition, the heart rate monitor may comprise a data transmission unit 130 for transmitting data to a data processing and control unit 150, which may be a PC, for example. The transmitter unit 100 comprises ECG electrodes 200, an ECG pre-amplification and pulse detection block 202, an inductance 204, and a power supply 208. The transmitter unit 100 may also comprise a charging part 206. From block 202, inductance is obtained, i.e. a pulse signal controlling the induction coil 204 and corresponding to the pulse. Consequently, a magnetic field that varies in synchronization with the pulse is generated in the inductance 204, and it enables inductive interaction between the inductance 204 and the induction coil 124 of the receiver unit 102, for example, and thus the transmitter unit 100 transfers the measured pulse to the receiver unit 102. The power supply 208 generates electric power for all blocks of the transmitter unit 100 (for the sake of clarity, power supply conductors are not shown in FIG. 3). If desired, the power supply 208 can also be charged by transfer of electric energy through the induction coil 204. The charging block 206 sees to it that charging does not disturb other operations.

The transmitter unit 100 may also comprise a memory, whereby the transmitter unit 100 does not necessarily need a receiver unit 102 as its pair; instead, the transmitter unit 100 stores its measurement data in the memory, from where the measurement data are fed for instance via the data transmission unit 130 to the computer 150 for processing and viewing.

The receiver unit 102 comprises a controlling control part 112. The control part 112 also controls an interface comprising selection means 114 and display means 116. The selection means 114 typically consist of a keyboard with which a user uses the receiver unit 102. The display means 116, such as an LCD display, display visual information to the user. The receiver unit may also comprise a light source 115 for illuminating the display 116 particularly in the dark, and an acoustic signaling device 117. The control part 112 is typically a microprocessor comprising a ROM memory 118A, in which the software controlling the device is stored. In addition, the device may comprise additional memory 118B, in which information generated during the measurement can be stored, e.g. information about the pulse, time data and other user-specific parameter information. The control part 112 may also be implemented using an ASIC circuit or other electronics components. The receiver 102 further comprises a transmission controller 120, receiver means 122 and an inductance 124. The transmission controller 120 generates data transmission from the receiver unit 102 to the data transmission unit 130 by using the inductance 124. The receiver means 122 use the inductance 124 to receive data as an induced voltage from the inductance 132 of the data transmission unit 130 and transforms it into digital for the microprocessor 112. The receiver means 122 constitute a part of the pulse detection block 202 or the like. The inductance 124, such as a coil, is tuned to the resonance of a capacitor (not shown in the figure) at the data transmission frequency used. The receiver unit 102 also comprises a power supply 128, which may be a battery, an accumulator, a rechargeable accumulator or the like. A charging part 126 attends to the charging of the rechargeable accumulator. The power supply 128 supplies electric power to all blocks of the receiver unit 102 (FIG. 3 does not show the power supply conductors). The power supply 128 may also be charged by transfer of electric energy via the induction coil 124. The charging block 126 sees to it that the charging takes place without interference.

The receiver unit 102, typically worn around the wrist as a wristwatch, is also independently able to measure the pulse with sensors 119. The measurement may take place optically and/or with a pressure sensor in accordance with prior art. In this case, the receiver unit 102 comprises substantially the functions of both the receiver 102 and the transmitter 100 and thus the separate transmitter unit 100 is not a necessary part of the measurement system.

The data transmission unit 130 comprises an inductance 132, a transmission controller 136, receiver means 138, a computational unit, such as a microprocessor 140, a memory 142, and an interface 144. The data transmission unit 130 communicates via the interface 144 with the data processing unit 150, such as a PC. The inductance 132 of the data transmission unit 130 is at the same resonance frequency as the inductance 124 of the receiver unit. The task of the transmission controller 136 is to generate a control signal for the inductance 132. The task of the receiver means 138 is to receive series-form data from the inductance 124 via the inductance 132. Data transmission may also take place by using other data transmission methods, known per se, such as an acoustic signal, an infrared signal or an RF signal. The microprocessor 140 converts the data transmission into a form suitable for the PC (the data processing unit 150). If need be, the memory 142 of the data transmission unit 130 can store the files read. The interface 144, e.g. RS 232, converts the voltage levels of the interface into suitable for the interface used. The power supply 128 supplies electric power to all blocks of the data transmission unit 130 (FIG. 3 does not show the power supply conductors). The power supply 134 may also be charged by transfer of electric energy via the induction coil 132. The charging block 133 sees to it that the charging takes place without interference. The sensors measuring the pulse may also be fastened to the handles or cover of a gym device, a game controller or the like, and when the handles or cover are seized by both hands, the sensors measure the pulse from an ECG signal between the hands.

Let us now study the measurement of mental load according to the solution presented, based on measuring a pulse parameter. The pulse parameter may be the heart rate HR or another value derived from the pulse and descriptive of the cardiac function or variation in the function within the measurement period. A suitable pulse parameter is the variation of the RR interval, HRV. The pulse parameter VHR may also be a proportioned pulse variation HRV, whereby the pulse variation HRV is divided by the heart rate HR. The pulse variation HRV is usually in the range from 10 to 100 ms, whereas the heart rate HR is usually between 30 and 200 beats per minute, corresponding to a pulse range of 2,000 ms to 300 ms. The pulse variation HRV is usually at its lowest when the pulse is at its highest and vice versa. Instead of or in addition to the heart rate, the proportioning factor may also be some other value characterizing the person being measured, e.g. age, sex, physical condition, etc.

In the solution presented, the person participating in the measurement performs at least two different cognitively loading tasks, the first task being based on reflexive action and the second task being based on the use of memory. The person participating in the measurement may perform the measurement on himself or the leader of the measurement may perform the measurement on the person being measured. The task based on reflexive action aims at loading the automatically occurring attention of the person being measured to a new stimulus. In this case, the task requires increased attention while the new stimulus is waited for. The reflexive task operates as the reference of the measurement. Tasks based on the use of memory require the division of attention in accordance with the will, and they measure the loading capacity level. The tasks are implemented as are game programs known from computers, for instance in the receiver unit 102 or the data processing and control unit 150 of the heart rate monitor. The tasks are displayed visually on the display and the participant in the measurement depresses the keys of the keyboard in the manner required by the task program.

The task based on reflexive action may be for instance an orientation task, e.g. a task of detecting a colored target, wherein the person participating in the measurement looks at the middle of a display. The display is divided for instance into two parts having different colors, and the target to be observed may instantaneously appear in the area of both parts. The person participating in the measurement reacts for instance by depressing a key of the measuring device or by saying out loud if the target flashed at the edge of the display had the same color as or a different color than the background, in whose area the target appeared. The colored target appears at varying intervals. Alternatively, the task based on reflexive action is such wherein a point is moving from the edge of the display towards a circle in the middle of the display. The person participating in the measurement has to depress a key of the measuring device when the point moves inside the circle. The principle in the reflexive task is that the participant in the measurement does not need learned facts; he only needs to react reflexively to the stimulus observed.

The task requiring memory could be the Stroop task, wherein memory is required to remember the name of a color. In the Stroop task, the person participating in the measurement is shown, on a display, names of colors, the names being written in different colors. The person participating in the measurement has to depress a button at the measuring device according to which color the name is written in. The person participating in the measurement may also speak the name of the color, and the measuring device records the name. In the Stroop task, the pulse variation HRV usually decreases as the level of difficulty increases. The level of difficulty is raised for instance by increasing the rate of occurrence of the names shown on the display. Instead of the Stroop task, other tasks based on the use of memory can also be used. The principle in tasks requiring memory is that the person participating in the measurement needs the memory or learned facts to perform the task, whereby the task loads the person participating in the measurement in a different manner than a task requiring reflexive action.

When the tasks are performed, they can be endlessly complicated for instance by accelerating the rate of occurrence of the information displayed to the person participating in the measurement. When the tasks are performed, the aim could be on the one hand to keep the errors or failures made by the person participating in the measurement at the desired level or within desired limits. This being so, the tasks are not for instance accelerated to a degree that the person participating in the measurement makes mostly mistakes; instead, the number of mistakes is kept at a constant level, e.g. at 10%, or within the desired limits, e.g. between 10% and 20%. In other words, the tasks are facilitated or complicated adaptively according to how large part of the efforts of the person participating in the measurement during the task are defined as erroneous (or alternatively correct).

In the solution presented, the pulse parameter of the person participating in the measurement is measured during both cognitively loading tasks. It is also possible to measure several different pulse parameters during both tasks. Once the measurements are made, the corresponding pulse parameters during the different cognitively loading tasks are compared with each other and a value descriptive of mental load is generated on the basis of the comparison of the pulse parameters.

Figure 4:
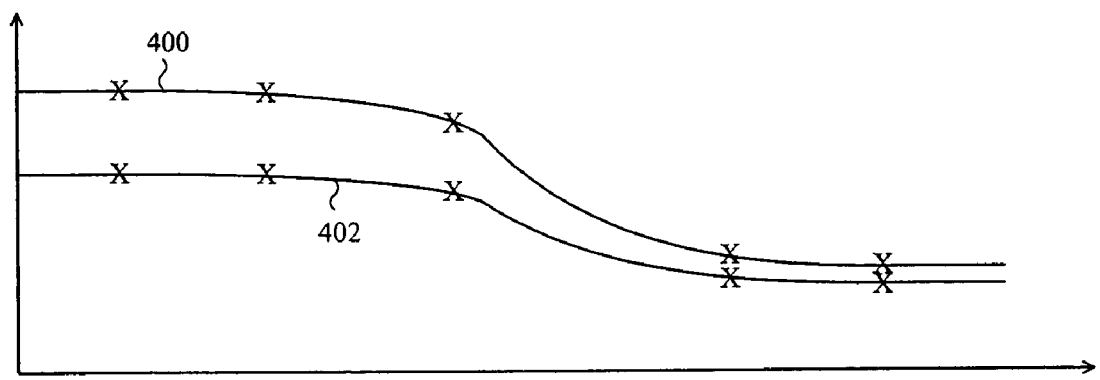
FIG. 4 shows pulse parameters during two different tasks on different days.

FIG. 4 shows corresponding pulse parameters during different cognitively loading tasks. The horizontal axis shows time in days and the vertical axis shows the value of the pulse variation $V_{RH}$=HRV/HR on a freely selected scale. Curve 400 shows the pulse variation according to a first task and curve 402 shows the pulse variation according to a second task. On measurement days 1 and 2, the difference in pulse variations during the execution of the different tasks is considerable, and this means that the person participating in the measurement experienced no mental load. To determine the magnitude of the difference between the pulse variations, the pulse variations can be compared with each other for instance by dividing the results by each other or by subtracting the pulse variations from each other. Let us assume that the value of the pulse variation of curve 400 on measurement days 1 and 2 is 1, and the pulse variation of curve 402 is 0.3. Thus, the obtained difference quotient descriptive of mental load is 3.33. On measurement day 3, the difference between the pulse variations has decreased, which is indicative of an increase in mental load. In this case, the pulse variation of curve 400 could be 0.5 and the pulse variation of curve 402 0.2, the difference quotient descriptive of mental load being 2.50. On measurement days 4 and 5, the difference between the pulse variations is at its smallest, and thus the mental load was considerable. The pulse variation of curve 400 could be 0.3 and the pulse variation of curve 402 could be 0.15, the difference quotient descriptive of mental load being 2.00. Generally, if the pulse parameters during the different tasks differ from each other less than a determined threshold value TH, the person participating in the measurement experiences mental load more than usual, and is stressed. If, again, the pulse parameters differ from each other more than the determined threshold value TH, the person participating in the measurement does not experience more mental load than usually. A suitable threshold value TH for the above calculation example could be 3, for example.

Figure 5:
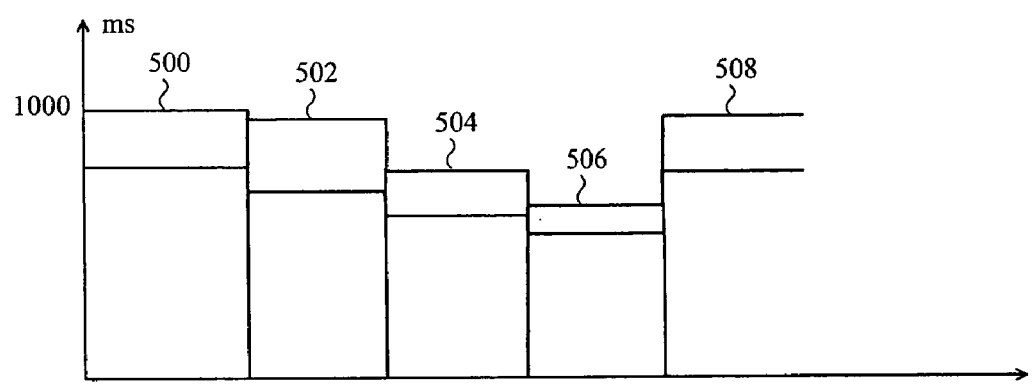
FIG. 5 shows pulse variation at rest and during different tasks.

FIG. 5 shows pulse intervals and the variation in pulse intervals during different tasks. The vertical axis shows time in milliseconds and the horizontal axis is divided according to the tasks. In step 500, the person participating in the measurement is resting calmly (e.g. sitting or lying down) for measurement of the initial level. In this case, the pulse rate is about 60 beats per minute and the pulse variation is about 50 ms. In step 502, the person participating in the measurement performs an orientation task, whereby the pulse rate does not change much, but the pulse variation increases to almost 100 ms. The task in step 502 is a reference measurement, with which the measurement of step 504 and, optionally, step 506 is compared. Step 504 involves an easy level of the Stroop task, the pulse rate increasing to about 85 beats a minute and the pulse variation dropping to about 50 ms. In step 506, the person performs a difficult level of the Stroop task, and the pulse rate is increased to 120 beats a minute. The pulse variation is now 30 ms. Finally, the final level is measured at rest in 508, wherein the pulse rate has dropped to about 60 beats a minute and the pulse variation has increased to about 50 ms.

In addition to these tasks, the person participating in the measurement may also perform a physical task. Here, for example, the person stands up from a sitting position. This change is shown similar to the transfer from step 500 to step 504 in FIG. 5, i.e. when sitting down, the pulse rate is low and the pulse variation fairly high, as in step 500. When the person stands up, the pulse rate increases and the pulse variation drops in the same way as in step 504. The physical task enables verification of the measurement of the mental load. If, for example, a slight change in the pulse variation is associated with the performance of both the cognitive and the physical task, this may be indicative of over-training or another state of fatigue associated with exercising and not (merely) mental load. If again a significant change in the pulse variation is associated with a physical task, the measurement of the mental load is as such independent of the physical exercise.

Figure 6:
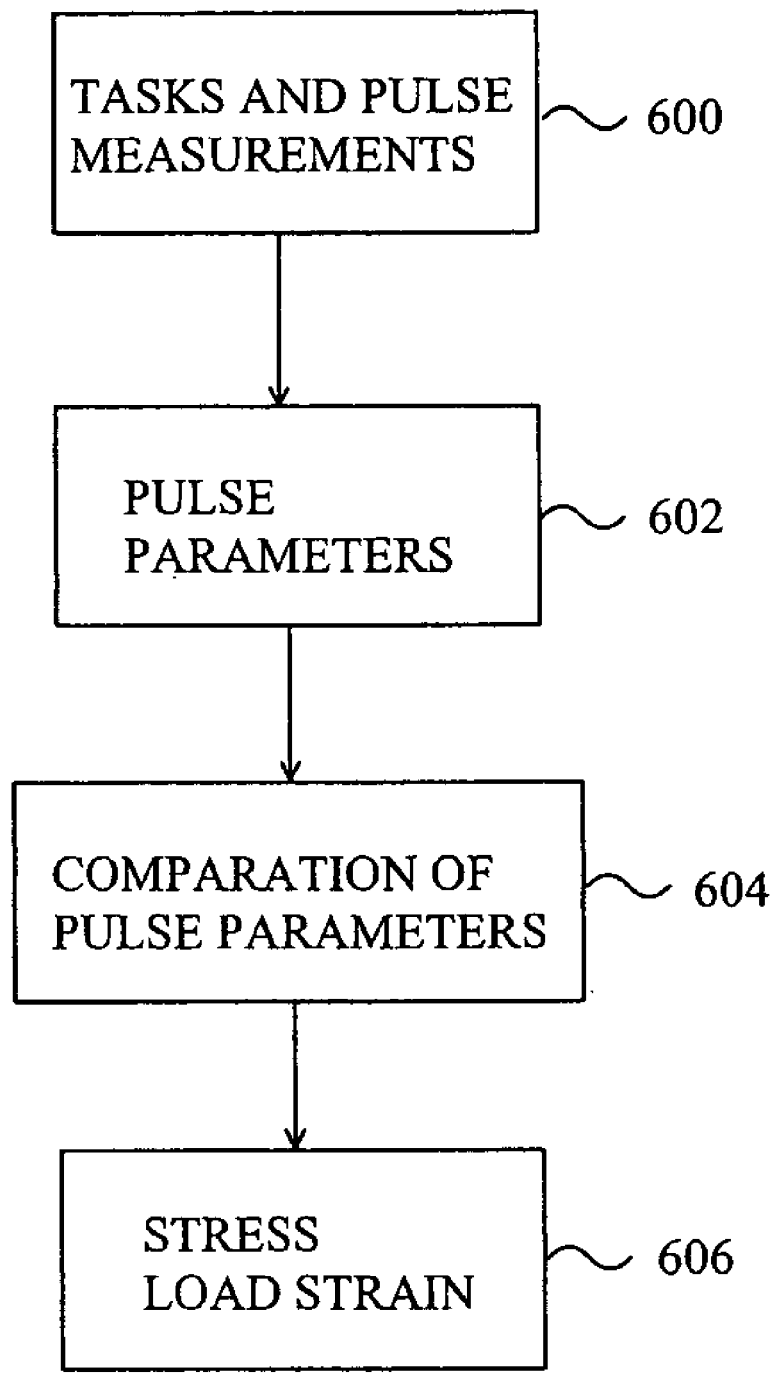
FIG. 6 is a flow diagram of a method.

FIG. 6 shows a flow diagram of the solution. In method step 600, the person participating in the measurement is provided with the tasks required in the measurement, and the pulse measurement during the tasks is carried out by using the transmission unit 100. The tasks are presented to the person being measured by using the receiver unit 102 in the data processing and control part 150 or in another unit of the electronic device, such as a mobile phone. The following method steps 602 to 606 are usually executed in the receiver unit 102, but they may also be carried out in the transmitter unit 100 or the data processing and control part 150. In method step 602, the instantaneous heart rate frequency HR and the heart rate variation HRV are generated on the basis of the frequency of occurrence of the QRS complexes present in the ECG signal. During the measurement, the signal may be modified for instance with a suitable digital filter by using high-pass filtering, for example. The pulse variation HRV may be generated by using for instance the standard deviation or variance of the RR intervals. The standard deviation s and the variation $s^2$ are expressed mathematically as follows:

$$s = \sqrt{\frac{1}{n-1}\sum_{j=1}^{n}(RR_j - \overline{RR})^2} \quad \text{and}$$

$$s^2 = \frac{1}{n-1}\sum_{j=1}^{n}(RR_j - \overline{RR})^2,$$

wherein n is the number of RR intervals, j is the index of the RR intervals, $RR_j$ is the $j^{th}$ value of an $\overline{RR}$ interval, and RR is the mean of the RR intervals. However, the pulse variation can be generated in many ways, and generally, pulse variation indeed refers to the division of the power of the QRS complexes as a function of the frequency of occurrence. This is why the pulse variation can also be measured as a value proportional to the magnitude of the total or partial power of the pulse spectrum. The pulse variation may also be calculated for instance by means of the height or width of the distribution pattern of the pulse variation or a magnitude derived from them. The measurement of the pulse spectrum may utilize Welch's averaged periodogram method for generating the power spectral density, an eigenvalue decomposition, such as the PMUSIC (Pseudospectrum using Multiple Signal Classification), the AR spectral decomposition (Auto Regressive Spectral Decomposition), the MSSD index (Mean Square Successive Difference), which is the square of squared differences that occur in the vicinity of normal RR intervals, Porges' filtering method or the like.

The pulse variation values during the tasks are stored as a function of time in either the transmitter unit 100, the receiver unit 102 or the data processing and control unit 150. The data stored in method step 604 are compared with each other, and, in method step 606, the mental load is determined. Usually, the pulse data are at least temporarily stored in the receiver unit 102, whose display can be used to display a curve according to FIG. 4, generated from the stored data, to the user of the heart rate monitor. Similarly, the amount of mental load can be displayed to the user as numbers and verbally.

Although the invention is described above with reference to the example according to the attached drawings, it is apparent that the invention is not limited thereto, but can be modified in a plurality of ways within the inventive idea disclosed in the appended claims.

What is claimed is:

1. A method of measuring mental load, the method comprising:
   measuring, by an electronic device, at least one pulse parameter;
   generating, by the electronic device, at least two different cognitively loading tasks for the person participating in the measurement, the first task determining a reference level and at least one other task determining the loading capacity level;
   determining, by the electronic device, at least two pulse parameters related to the at least two different cognitively loading tasks for the person participating in the measurement;
   comparing, by the electronic device, the pulse parameters during the different tasks with each other; and
   generating, by the electronic device, a value descriptive of the mental load of the person participating in the measurement on the basis of the comparison of the pulse parameters, the first task used to determine the reference level being based on reflexive action and the at least one other task used to determine the loading capacity level being based on the use of memory.

2. A method as claimed in claim 1, the method further comprising measuring the heart rate variation as the pulse parameter.

3. A method of measuring mental load, the method comprising:
   measuring, by an electronic device, at least one pulse parameter;
   generating, by the electronic device, at least two different cognitively loading tasks for the person participating in the measurement, the first task determining a reference level and at least one other task determining the loading capacity level;
   determining, by the electronic device, at least two pulse parameters related to the at least two different cognitively loading tasks for the person participating in the measurement;
   comparing, by the electronic device, the pulse parameters during the different tasks with each other;
   generating, by the electronic device, a value descriptive of the mental load of the person participating in the measurement on the basis of the comparison of the pulse parameters; and
   measuring the ratio of the heart rate variation to the heart beat rate as the pulse parameter.

4. A method of measuring mental load, the method comprising:
   measuring, by an electronic device, at least one pulse parameter;
   generating, by the electronic device, at least two different cognitively loading tasks for the person participating in the measurement, the first task determining a reference level and at least one other task determining the loading capacity level;
   determining, by the electronic device, at least two pulse parameters related to the at least two different cogni- tively loading tasks for the person participating in the measurement;
   comparing, by the electronic device, the pulse parameters during the different tasks with each other;
   generating, by the electronic device, a value descriptive of the mental load of the person participating in the measurement on the basis of the comparison of the pulse parameters; and
   using two cognitively loading tasks, the first task used to determine the reference level being an orientation task and the second task used to determine the loading capacity level being a Stroop task.

5. A method as claimed in claim 1, the method further comprising seeking for a task loading capacity that keeps the number of errors performed by the person participating in the measurement within the desired limits during the tasks.

6. A method of measuring mental load, the method comprising:
   measuring, by an electronic device, at least one pulse parameter;
   generating, by the electronic device, at least two different cognitively loading tasks for the person participating in the measurement, the first task determining a reference level and at least one other task determining the loading capacity level;
   determining, by the electronic device, at least two pulse parameters related to the at least two different cognitively loading tasks for the person participating in the measurement;
   comparing, by the electronic device, the pulse parameters during the different tasks with each other;
   generating, by the electronic device, a value descriptive of the mental load of the person participating in the measurement on the basis of the comparison of the pulse parameters; and
   measuring, before performance of the cognitive tasks, an initial level associated with rest, and, after the tasks, a final level associated with rest such that the person participating in the measurement is quietly in position during the measurement of both the initial level and the final level, and by correcting the measuring result of mental load according to the measured initial level and final level.

7. A method of measuring mental load, the method comprising:
   measuring, by an electronic device, at least one pulse parameter;
   generating, by the electronic device, at least two different cognitively loading tasks for the person participating in the measurement, the first task determining a reference level and at least one other task determining the loading capacity level;
   determining, by the electronic device, at least two pulse parameters related to the at least two different cognitively loading tasks for the person participating in the measurement;
   comparing, by the electronic device, the pulse parameters during the different tasks with each other;
   generating, by the electronic device, a value descriptive of the mental load of the person participating in the measurement on the basis of the comparison of the pulse parameters; and
   measuring the pulse variation during at least one physically loading task and correcting the measuring result of mental load according to the result obtained from at least one physically loading task.

8. A method as claimed in claim 1, the method further comprising loading cognitively the person being measured by a receiver unit of a heart rate monitor and generating a value descriptive of the mental load of the person participating in the measurement on the basis of a comparison of the pulse parameters.

9. A method as claimed in claim 1, the method further comprising loading, by the means for loading of the electronic device, the person being measured with at least two different cognitively loading tasks, and generating, by the receiver unit of the heart rate monitor, a value descriptive of the mental load of the person participating in the measurement on the basis of a comparison of the pulse parameters.

10. An electronic device for measuring mental load, the electronic device comprising:

a heart rate monitor including means for measuring at least one pulse parameter;

means for loading the person to be measured with at least two different cognitively loading tasks, the first task determining a reference level and at least one other task determining the loading capacity level, wherein the electronic device is arranged to determine at least two pulse parameters related to the at least two different cognitively loading tasks for the person participating in the measurement, compare the pulse parameters during the different tasks with each other, and generate a value descriptive of the mental load of the person participating in the measurement on the basis of the comparison of the pulse parameters, the first task used to determine the reference level being based on reflexive action and the at least one other task used to determine the loading capacity level being based on the use of memory.

11. An electronic device as claimed in claim 10, wherein the means for loading the person to be measured with at least two different cognitively loading tasks are part of the heart rate monitor.

12. An electronic device as claimed in claim 10, wherein the electronic device is arranged to measure the heart rate variation as the pulse parameter.

13. An electronic device for measuring mental load, the electronic device comprising:

a heart rate monitor including means for measuring at least one pulse parameter;

means for loading the person to be measured with at least two different cognitively loading tasks, the first task determining a reference level and at least one other task determining the loading capacity level, wherein the electronic device is arranged to determine at least two pulse parameters related to the at least two different cognitively loading tasks for the person participating in the measurement, compare the pulse parameters during the different tasks with each other, and generate a value descriptive of the mental load of the person participating in the measurement on the basis of the comparison of the pulse parameters, wherein the electronic device is arranged to measure the ratio of the heart rate variation to the heart beat rate as the pulse parameter.

14. An electronic device for measuring mental load, the electronic device comprising:

a heart rate monitor including means for measuring at least one pulse parameter;

means for loading the person to be measured with at least two different cognitively loading tasks, the first task determining a reference level and at least one other task determining the loading capacity level, wherein the electronic device is arranged to determine at least two pulse parameters related to the at least two different cognitively loading tasks for the person participating in the measurement, compare the pulse parameters during the different tasks with each other, and generate a value descriptive of the mental load of the person participating in the measurement on the basis of the comparison of the pulse parameters, wherein the first task used to determine the reference level is an orientation task and the at least one other task used to determine the loading capacity level is a Stroop task.

15. An electronic device as claimed in claim 10, wherein the electronic device is arranged to seek for a task loading capacity that keeps the number of errors performed by the person participating in the measurement within the desired limits during the tasks.

16. An electronic device for measuring mental load, the electronic device comprising:

a heart rate monitor including means for measuring at least one pulse parameter;

means for loading the person to be measured with at least two different cognitively loading tasks, the first task determining a reference level and at least one other task determining the loading capacity level, wherein the electronic device is arranged to determine at least two pulse parameters related to the at least two different cognitively loading tasks for the person participating in the measurement, compare the pulse parameters during the different tasks with each other, and generate a value descriptive of the mental load of the person participating in the measurement on the basis of the comparison of the pulse parameters, wherein the electronic device is arranged to measure an initial level associated with rest prior to performing the tasks, and a final level associated with rest after the tasks such that the person participating in the measurement is quietly in position during the rest, and to correct the measuring result of mental load according to the measured initial level and final level.

17. An electronic device for measuring mental load, the electronic device comprising:

a heart rate monitor including means for measuring at least one pulse parameter;

means for loading the person to be measured with at least two different cognitively loading tasks, the first task determining a reference level and at least one other task determining the loading capacity level, wherein the electronic device is arranged to determine at least two pulse parameters related to the at least two different cognitively loading tasks for the person participating in the measurement, compare the pulse parameters during the different tasks with each other, and generate a value descriptive of the mental load of the person participating in the measurement on the basis of the comparison of the pulse parameters, wherein the electronic device is further arranged to measure the pulse variation during at least one physically loading task and by correcting the measuring result of mental load according to the result obtained from the physically loading task.

18. An electronic device as claimed in claim 10, wherein the electronic device is a heart rate monitor comprising a receiver unit for cognitively loading the person being measured and for generating a value descriptive of the mental load of the person participating in the measurement on the basis of the comparison of the pulse parameters.

19. An electronic device as claimed in claim 10, wherein the electronic device comprises means for cognitively loading the person being measured and a heart rate monitor receiver unit for generating a value descriptive of the mental load of the person participating in the measurement on the basis of the comparison of the pulse parameters.

* * * * *